US006437186B1

(12) United States Patent
Ostgard et al.

(10) Patent No.: US 6,437,186 B1
(45) Date of Patent: Aug. 20, 2002

(54) PROCESS FOR THE PREPARATION OF 3-AMINOMETHYL-3,5,5-TRIMETHYLCYCLOHEXYLAMINE

(75) Inventors: Daniel Ostgard, Kleinostheim; Monika Berweiler, Maintal; Stefan Roder, Sinntal, all of (DE); Jorg Sauer, Mobile, AL (US); Bernd Jaeger, Darmstadt (DE); Norbert Finke, Oer-Erkenschwick (DE); Christian Lettmann, Essen (DE)

(73) Assignee: Degussa AG, Hanau (DE)

( * ) Notice: Subject to any disclaimer, the term of this patent is extended or adjusted under 35 U.S.C. 154(b) by 0 days.

(21) Appl. No.: 10/020,914

(22) Filed: Dec. 19, 2001

(30) Foreign Application Priority Data

Dec. 23, 2000 (DE) .......................... 100 65 030

(51) Int. Cl.[7] ............................................. C07C 209/00
(52) U.S. Cl. ........................ 564/448; 564/453; 564/461
(58) Field of Search ................................ 564/453, 448, 564/461

(56) References Cited

U.S. PATENT DOCUMENTS 4,153,578 A    5/1979    DeThomas et al.

FOREIGN PATENT DOCUMENTS

| DE | 2053799 A | 6/1971 |
|---|---|---|
| DE | 2101856 A | 7/1972 |
| DE | 2100373 A | 9/1972 |
| DE | 3942371 A1 | 6/1991 |
| DE | 4426472 A1 | 2/1995 |
| DE | 19540191 C1 | 11/1996 |
| DE | 19627265 A1 | of 1998 |
| DE | 19933450 A1 | 1/2001 |
| EP | 0042119 A | 12/1981 |
| EP | 0449089 A | 10/1991 |
| EP | 0880996 A1 | 12/1998 |

*Primary Examiner*—Samuel Barts
(74) *Attorney, Agent, or Firm*—Venable

(57) ABSTRACT

Process for the preparation of isophorone diamine from isophorone nitrile, isophorone nitrilimine or mixtures containing isophorone nitrile and/or isophorone nitrilimine by hydrogenation through to amine in the presence of at least ammonia, hydrogen and a formed Raney hydrogenation catalyst based on cobalt, nickel, copper and/or iron, wherein the Raney catalyst is present in the form of hollow bodies.

21 Claims, No Drawings

PROCESS FOR THE PREPARATION OF 3-AMINOMETHYL-3,5,5-TRIMETHYLCYCLOHEXYLAMINE

The invention relates to an improved process for the preparation of 3-aminomethyl-3,5,5-trimethylcyclohexylamine, hereinbelow also named isophorone diamine or abbreviated to IPDA, from 3-cyano-3,5,5-trimethylcyclohexanone, hereinbelow also named isophorone nitrile or abbreviated to IPN, by hydrogenation through to amine in the presence of a formed Raney hydrogenation catalyst based on cobalt. The invention preferably includes a first stage for the at least partial conversion of isophorone nitrile into isophorone nitrilimine and a second stage for the hydrogenation of the reaction mixture through to amine in the presence of a fixed-bed Raney hydrogenation catalyst based on cobalt. The process enables isophorone diamine to be prepared at yields as high as or higher than those of the methods known hitherto while simultaneously utilising markedly lower quantities of catalyst.

Isophorone diamine is used as a starting material for the preparation of isophorone diisocyanate, as an isocyanate component for polyurethane systems, as an amine component for polyamides and as a curing agent for epoxy resins. Isophorone diamine is in many instances prepared from isophorone nitrile, with the carbonyl group being converted into an amino group and the nitrile group into an aminomethyl group in the presence of ammonia, hydrogen and hydrogenation catalysts. The starting material, isophorone nitrile can be obtained in known manner by an addition reaction between hydrogen cyanide and isophorone (q.v. Example, DE-OS 39 42 371, for example).

Raney catalysts based on cobalt are frequently preferred because of their good catalytic properties in the synthesis of isophorone diamine from isophorone nitrile or isophorone nitrilimine and their substantially simpler preparation in comparison with supported catalysts.

Raney catalysts, also known as activated metal catalysts, comprise an alloy of at least one catalytically active metal and at least one alkali-leachable metal. Aluminium is predominantly utilised for the alkali-soluble alloy component, but other metals such as, for example, zinc and silicon are also usable. The leachable component is dissolved out by the addition of alkali to the alloy, thus activating the catalyst.

Powdered catalysts have the disadvantage of being utilisable only in a batch process and requiring costly separation from the reaction media after the catalytic reaction. For this reason, among others, it is preferable to carry out the preparation of isophorone diamine in continuous processes. This requires fixed-bed catalysts which, in addition to having good catalytic activity, must also be sufficiently strong for continuous operation.

Patent specification DE 195 40 191 describes a two-stage process for the preparation of isophorone diamine. In this process isophorone nitrile is first converted with ammonia into the corresponding imine in the presence or in the absence of an imination catalyst, and the product mixture which is obtained is hydrogenated to isophorone diamine with the addition of hydrogen. A formed Raney catalyst based on cobalt serves as the hydrogenation catalyst. In addition to the catalyst alloy of cobalt and aluminium, the catalyst also contains further metallic cobalt which, as a binder, ensures the necessary stability of the formed body. The disadvantage of this process is that the cobalt added as the binder has only low catalytic activity, thus reducing the activity of the catalyst below that of binder-free catalysts. As a result the amount of catalyst or of the metal cobalt required is relatively large. The result is high capital costs for the cobalt as well as for reactor design, occasioned, for example, by the great weight of the catalysts.

This disadvantage is avoided in the preparation of isophorone diamine as described in document EP 0 880 996. For the hydrogenation a formed cobalt catalyst of the Raney type is used which, before activation by leaching of the aluminium, comprises exclusively a cobalt-aluminium alloy. This catalyst has the advantage over the catalyst used in document DE 19540191 of a markedly lower bulk density of only 1.2 kg/l. Despite the lower bulk density, the hydrogenation with the catalyst comprising exclusively the catalyst alloy leads to slightly higher yields for the same catalyst mass. The disadvantage of the method described in EP 0 880 996 lies in the fact that the catalyst used, however, still has very high bulk densities, relative to the catalyst according to the invention.

Document DE 199 33 450.1 describes metal catalysts which are present in the form of hollow bodies, preferably in the form of hollow spheres. These catalysts have a low bulk density of from 0.3 to 1.3 g/ml. In addition to the catalysts, their use in hydrogenation reactions is furthermore claimed. The Examples mention activity tests in respect of the hydrogenation of nitrobenzene to aniline, in which when the hollow spherical catalysts are used, hydrogen consumption, and hence the activity of the catalyst, is markedly higher per gramme of catalyst than when a comparison catalyst is used. However, the preparation of isophorone diamine with use of the catalysts described is not mentioned as such.

The object of the present invention is therefore to develop a process for the preparation of isophorone diamine from isophorone nitrile, in which the hydrogenation through to amine is carried out with a fixed-bed Raney hydrogenation catalyst which, while having a substantially lower bulk density than comparable catalysts, has the same or better hydrogenating activity. It is a further aim of the invention to achieve the same or better conversion rates of isophorone nitrile or isophorone nitrilimine, while utilising less catalyst material than in known processes.

The invention on which this rests has surprisingly shown that with the preparation of isophorone diamine from isophorone nitrilimine or isophorone nitrile by hydrogenation through to amine with the aid of the hollow-body-form catalysts (preferably cobalt catalysts) of the Raney type described in the document DE 199 33 450.1 markedly higher conversion rates can be obtained per unit of mass of catalyst than with comparable catalysts. This observation is surprising inasmuch as it cannot necessarily be taken that the hollow-body-form (cobalt) catalyst reaches the required activities in the specific case of the hydrogenation of isophorone nitrile or isophorone nitrilimine.

The invention provides a process for the preparation of isophorone diamine by hydrogenation through to amine of mixtures containing isophorone nitrile or isophorone nitrilimine in the presence of at least ammonia and hydrogen, in which a formed Raney hydrogenation catalyst is used as the hydrogenation catalyst, which is characterised in that the Raney catalyst is present in the form of hollow bodies.

In one embodiment of the invention a Raney catalyst based on cobalt and/or based on nickel and/or based on copper and/or iron may be used as the Raney catalyst.

This process has the advantage that isophorone diamine can be prepared with markedly less catalyst material but at conversion rates the same as or better than has been possible hitherto in accordance with the prior art.

The advantage on which this invention is based is achieved by the use of Raney catalysts in the form of hollow bodies, in particular on the basis of cobalt and/or on the basis of nickel and/or on the basis of copper and/or iron. The catalysts used in the process according to the invention may be prepared in accordance with the method described in DE 199 33 450.1. In accordance with this method, for example, a mixture of a cobalt alloy powder with a leachable metal, preferably aluminium, an organic binder and optionally water as well as promoters is applied to spheres prepared from a thermally removable material. Expanded polystyrene spheres may preferably be used. The mixture containing the metal alloy may preferably be applied to the polymer spheres in a fluidised bed. From 0.0–10 wt. % polyvinyl alcohol and/or from 0.0–3 wt. % glycerol may preferably be utilised as the organic binders. The coated expanded polymer spheres are then calcined at temperatures greater than 300° C., preferably temperatures within the range 450° C. to 1300° C., in order to thermally remove the expanded polymer and sinter the metal. The hollow bodies acquire a more stable form in this manner. After calcining, the hollow-body-form catalysts are activated by treatment with basic solutions, preferably alkali or alkaline earth hydroxides in water, even more preferably aqueous sodium hydroxide solution. The catalysts thus obtained have bulk densities of between 0.2 and 2.0 kg/l, preferably 0.3 and 1.3 kg/l.

According to the invention, the catalysts used in the process have the form of hollow bodies. In a preferred embodiment, the Raney catalysts are present as hollow spheres. Hollow spheres are conventionally simple to prepare and have a high breaking resistance.

After calcining and before activation the hollow-body-form catalysts used according to the invention preferably no longer contain binders. It is, however, also possible that an inorganic binder is still contained.

The bulk density of the Raney catalysts used may be from 0.3 g/ml to 1.3 g/ml.

The catalyst bodies used may have a diameter of from 0.5 to 20 mm. They may have a shell thickness of from 0.1 to 7.0 mm.

The cobalt, nickel, copper and/or iron alloy of the catalysts used according to the invention is preferably composed of 20–80 wt. % cobalt, nickel, copper and/or iron and 20–80 wt. % of an alkali-leachable metal, preferably aluminium. A rapidly or slowly cooled cobalt, nickel, copper and/or iron alloy may be used as the cobalt, nickel, copper and/or iron alloy. Rapid cooling is understood to mean, for example, cooling at a rate of from 10 to $10^5$ K/s. Cooling media may be various gases or liquids such as, for example, water. Slow cooling is understood to refer to methods having lower cooling rates.

In the process according to the invention hollow-body-form cobalt, nickel, copper and/or iron catalysts doped with other metals may be used. The doping metals are frequently also known as promoters. The doping of Raney catalysts is described, for example, in documents U.S. Pat. No. 4,153, 578, DE 21 01 856, DE 21 00 373 and DE 20 53 799. Preferred metals for doping are elements in Groups 1A, 2A, 2B, 3B to 7B, 8, 1B, 2B and/or 3A of the Periodic Table as well as germanium, tin, lead, antimony and/or bismuth. Chromium, manganese, iron, vanadium, tantalum, titanium, tungsten, molybdenum, rhenium and/or metals in the platinum group are particularly preferred. The promoter content of the catalyst may be from 0.0001 to 50 wt. %, preferably 0.001 to 20 wt. %. The promoters may be contained already as constituents of the alloy or they may be added only at a subsequent time, in particular after activation.

In the process according to the invention hollow-body-form catalysts having a diameter of from 0.5 to 20 mm and a shell thickness of from 0.05 to 7 mm are preferably used. The catalyst shells may be impermeable, or they may have a porosity of from 0% to 80% or higher.

The hollow-body-form catalysts used in the process according to the invention may comprise one or more layers. If the catalyst bodies have a plurality of layers, the bodies are dried in between the individual coating steps, during preparation. This is preferably carried out on a fluidised bed at temperatures of from 60 to 150° C.

During the process according to the invention the hollow-body-form cobalt, nickel, copper and/or iron catalysts of the Raney type are utilised in the activated form. In the activated state the leachable metal which was present in the non-activated catalyst bodies may have been leached wholly or only partially with alkalis.

In the process according to the invention for the preparation of isophorone diamine the hollow-body-form cobalt, nickel, copper and/or iron catalyst described is utilised for the step of hydrogenation through to amine of isophorone nitrile or of isophorone nitrilimine. This process may be carried out in batch-wise or continuous manner.

It is possible to carry out the process according to the invention in one stage or in a plurality of stages. If the process is carried out in one stage, isophorone nitrile is hydrogenated through to amine directly in the presence of ammonia, hydrogen, the hollow-body-form cobalt catalyst and optionally further additives and in the presence or in the absence of organic solvents. The term "in a plurality of stages" means that isophorone nitrile is first converted wholly or partially into isophorone nitrilimine in a separate reactor or reactor section, and this isophorone nitrilimine, as a pure substance or in a mixture with other components, is hydrogenated through to amine in the presence of ammonia. The use of the hollow-body-form cobalt, nickel, copper and/or iron catalyst, which is essential to the invention, is important in the hydrogenation through to amine.

The reaction conditions, that is to say pressure and temperature, as well as the ratio of IPN, $NH_3$, hydrogen and optionally the organic solvent, are identical in the single-stage and the two-stage operation and correspond to the conditions of the hydrogenation stage in the two-stage operation.

A preferred embodiment of the process according to the invention for the preparation of isophorone diamine is a two-stage process: in the first stage, at least part of the isophorone nitrile utilised is converted into isophorone nitrilimine in the presence or in the absence of an imination catalyst and/or of solvents. The ratio of isophorone nitrilimine to isophorone nitrile should be greater than 1, preferably greater than 4 and even more preferably greater than 9 after the imination. In the second stage the reaction product of the first stage, either as it arises or following a further treatment, is hydrogenated through to amine in the presence of at least ammonia and hydrogen and in the presence or in the absence of an organic solvent at a temperature of from 20 to 150° C., preferably 60 to 150° C., and at a pressure of from 0.3 to 50 MPa, preferably 5 to 10 MPa, hydrogenated optionally with the aid of hollow-body-form cobalt, nickel, copper and/or iron catalysts.

The imination may be carried out in the presence or in the absence of an imination catalyst. Where the imination is carried out in the absence of an imination catalyst, a number of hours are required at a reaction temperature within the range 10 to approx. 60° C. in order to achieve the desired degree of imination. At higher temperatures there is a risk of increased by-product formation, which would severely affect the purity of the end product isophorone diamine. Further working-up and purification steps would be necessary.

In order to accelerate the establishment of equilibrium by the imination reaction, it is expedient to use an imination catalyst. The imination catalysts known from the prior art may be used for this purpose. Suitable catalysts are, for example, inorganic or organic ion exchangers (q.v. EP 0 042 119), support-bound hetero-polyacids (q.v. DE 44 26 472), acid metal oxides, in particular aluminium oxide and titanium dioxide (anatase) (q.v. EP 0 449 089), organopolysiloxanes containing sulfonic acid groups (DE 196 27 265.3), and acid zeolites. If an imination catalyst is used, the reaction temperature may be between 10 and 150° C., preferably between 30 and 130° C. and in particular between 40 and 120° C. The imination reaction is preferably carried out at pressures within the range atmospheric pressure to 50 MPa, preferably at pressures up to 30 MPa. That pressure at which the subsequent hydrogenation is also carried out is particularly preferred.

Although isophorone nitrile can be iminated with liquid ammonia in the absence of a further solvent, it may be advantageous to use additionally a solvent from the series of an alcohol having 1 to 4 C atoms, preferably of a monohydric primary alcohol and in particular methanol, or an ether such as tetrahydrofuran, MTBE (=methyl-tert.-butylether) or dioxane. A mixture containing isophorone nitrile, liquid ammonia and methanol is preferably supplied to the imination reactor. The mixture expediently contains from 10 to 40 wt. %, preferably 10 to 30 wt. %, isophorone nitrile and from 10 to 40 wt. %, preferably 20 to 40 wt. %, ammonia. It is advantageous to mix together isophorone nitrile, ammonia and the solvent in a ratio such as to result in a substantially homogeneous mixture. It is in principle also possible to undercut or exceed the aforementioned limit values, provided that a substantially homogeneous solution arises in this case. The use of the organic solvent enables the imination reaction to be carried out at pressures lower than would be possible in the absence of the solvent. The preferred pressures are within the range 2 to 10 MPa when the solvent is present.

In the imination in the presence of an imination catalyst the catalyst may be used in the form of a suspension catalyst or a fixed-bed catalyst. The use of a fixed-bed catalyst is advantageous because in this case costly steps to separate the reaction mixture from the catalyst are superfluous. When isophorone nitrite is iminated in the presence of a fixed-bed catalyst, the latter is utilised in the form of conventional formed catalyst pieces such as pressed rods, pellets and tablets as the bed in a fixed-bed reactor. The imination catalyst may be arranged in a dedicated reactor. It is, however, also possible to arrange the imination catalyst in a reactor which contains both a bed of the imination catalyst and a bed of the catalyst utilised for the hydrogenation through to amine. Depending on whether the reactor is operated as a trickle-bed reactor or a bubble reactor, the bed of the imination catalyst is situated either above (trickle-bed reactor) or below (bubble reactor) the bed of hydrogenation catalyst. It is also possible to use a single reactor which contains not only a bed of the hydrogenation catalyst but also a bed of the imination catalyst. In this case the two stages of the isophorone diamine synthesis proceed in one reactor but in two discrete reactor sections.

Such a reactor is preferably operated in the form of a trickle-bed reactor. In this case the mixture of isophorone nitrile, ammonia and solvent, in particular alcohol and/or ether, is fed at the reactor head. In these cases hydrogen for the hydrogenation through to amine expediently flows simultaneously into the reactor from above.

In addition to the aforementioned constituents of the mixture which is to be supplied to the imination stage, the mixture may contain additionally fractions, which boil at higher or lower temperatures than isophorone diamine, from the working-up by distillation of the reaction mixture removed from the trickle-bed reactor. Such fractions may also contain, in addition to isophorone residues, by-products such as those from which isophorone diamine forms again under the reaction conditions. The isophorone diamine yield can be markedly increased by recirculating such fractions into the mixture which is to be utilised. It is particularly advantageous to supply to the trickle-bed reactor, together with the mixture of isophorone nitrile, ammonia and solvent, preferably methanol and/or MTBE, the fraction which boils at temperatures above isophorone diamine, which in addition to isophorone diamine residues contains 3,3,5-trimethyl-6-imino-7-azabicyclo[3,2,1]octane as the principal product. It is possible by recirculating the fraction containing the aforementioned by-product—a bicyclic compound of amidine structure—to increase the isophorone diamine yield appreciably and hence improve the economics of the process. The fraction containing the bicyclic amidine may, if desired, also be added directly to the reaction mixture which is to be supplied to the second stage.

The decisive improvement in the process according to the invention resides in the use, in the hydrogenation through to amine, of the hollow-body-form cobalt, nickel, copper and/or iron catalysts already described. In the preferred two-stage process a mixture containing isophorone nitrilimine is hydrogenated with the aid of the hollow-body-form cobalt, nickel, copper and/or iron catalyst. The mixture indicated may be directly that which is obtained in the imination of isophorone nitrile with ammonia in the presence or in the absence of an organic solvent such as, for example, methanol and/or MTBE, in the presence or in the absence of an imination catalyst, or that which is obtainable from such a reaction mixture after the addition or the removal by distillation of solvents and/or of part of the ammonia. Here, the continuously operated hydrogenation in a fixed-bed reactor is preferred for the same reasons as have already been indicated in the case of the imination, however a batch operation or carrying out the process in a stirred-tank reactor cascade are also possible. As has already been discussed in the case of the imination reaction, the reactor may be operated both as a trickle-bed reactor and also a bubble column, with trickle-bed operation being, however, preferred.

It is preferred that in the step of hydrogenation through to amine the mixture containing the isophorone nitrilimine should contain an organic solvent, preferably an aliphatic $C_1$ to $C_4$ alcohol, in particular methanol, or an ether, in particular MTBE or tetrahydrofuran. It is possible in this case to carry out the hydrogenation through to amine at lower pressures than when no such solvent is present. Provided that no organic solvent was yet contained in the reaction mixture when the imination was carried out in the first step, the organic solvent, preferably methanol or MTBE, may also be added to the reaction mixture which is to be hydrogenated through to amine. It is, however, also possible to work without the addition of a solvent.

It is also possible to connect a plurality of trickle-bed reactors in series for the hydrogenation, with the reaction mixture leaving the first reactor being fed again at the head of the second reactor. It is possible using this method to further subdivide the hydrogenation step. The construction and operation of such reactors is known from the prior art.

The hydrogen necessary for the hydrogenation may be supplied to the reactor either in excess, for example up to 10000 molar equivalents, or in a quantity such that it is unnecessary to remove and recycle hydrogen from the reactor. If a solvent is present in the reaction mixture hydrogen is preferably not supplied in excess, in order to avoid the cost of the engineering required to separate this excess and condense the ammonia and solvent contained therein as well as compress the purified hydrogen. If the reaction mixture contains no solvent, the hydrogenation through to amine may be carried out with a hydrogen excess of from 1 to 30 molar equivalents. If the process according to the invention is carried out in a continuous process, the hydrogen may be supplied in co-current or counter-current.

If the reaction mixture in the hydrogenation through to amine according to the preferred embodiment contains a solvent, for example MTBE or methanol, the hydrogenation through to amine, thus the second reaction step, may normally be carried out at a temperature within the range 20 to 150° C., preferably 90 to 130° C., and at a pressure within the range 0.3 to 10 MPa, preferably 5 to 8 MPa and in particular 8 MPa. Owing to the moderate operating pressures indicated which are possible when the preferred mixtures of isophorone nitrile, ammonia, hydrogen and solvent are used under the temperature conditions indicated, the capital cost is lower and the economics are hence improved over those of processes which require a high operating pressure. The indicated pressure is understood to be the total pressure which is composed of the partial pressures of ammonia, hydrogen, $C_1$ to $C_4$ alcohol and the remaining constituents of the reaction mixture. It is, however, also possible to carry out the hydrogenation through to amine within different temperature or pressure ranges such as, for example, between 150 and 250° C. or at pressures of up to 50 MPa, for example if the reaction mixture contains no organic solvent.

Two different stereoisomers may be formed in the hydrogenation of isophorone nitrile or isophorone nitrilimine. It may be preferable to influence the isomer ratio by the selection of a temperature programme in the hydrogenation stage. It is, for example, possible to hydrogenate a mixture containing isophorone nitrile or isophorone nitrilimine initially at a temperature within the range 20 to 90° C., and in a consecutive section at a temperature within the range 90 to 150° C., wherein the temperature difference between the two hydrogenation sections should be at least 30° C. Such a temperature programme in the hydrogenation may be achieved, for example, by dividing the hydrogenation stage into two sub-sections having discrete reactors. It is possible in this manner to shift the selectivity in favour of the cis isomer.

The hydrogenation through to amine is carried out in the presence of ammonia. 2 or more mole ammonia, generally from 5 to 500 mole ammonia, are normally utilised per mole nitrile or imine. The ammonia supply which was adjusted in the immediately preceding preparation of isophorone nitrilimine may expediently be selected. Ammonia serves partially or—in the absence of another solvent such as methanol or tetrahydrofuran—also wholly as a solvent, as well as serving for the imination.

The required volume of fixed-bed catalyst for the hydrogenation stage is determined in accordance with the LHSV value (liquid hour space velocity) which is dependent on the operating pressure, temperature and catalyst activity, and which must be observed in order to obtain as close to quantitative a conversion of the mixture containing isophorone nitrilimine and isophorone nitrile as possible. The LHSV value when the preferred mixtures of isophorone nitrile, ammonia, hydrogen and solvent are used is normally at least 0.5 $h^{-1}$ and is preferably within the range 1 $h^{-1}$ to 4 $h^{-1}$ and even more preferably at about 2 $h^{-1}$ to 3 $h^{-1}$.

The reaction mixture leaving the hydrogenation reactor is worked up in a manner which is known per se. This working-up normally includes separation of the ammonia, the solvent or mixtures of ammonia and solvent, if solvents are present, as well as isolation of the IPD.

Irrespective of whether or not the process according to the invention for the preparation of isophorone diamine is carried out in a preferred embodiment, one or more hydroxide bases may also be added when a mixture of isophorone nitrile, ammonia, hydrogen and optionally a solvent is reacted.

A frequent side-reaction when hydrogenating nitrites is the formation of secondary amines. This is due to an exchange of the imino function, in which, by displacement of ammonia from the intermediate stage of the imine which the hydrogenation passes through, primary amine which has already formed forms a new, n-alkylated imine which is then hydrogenated further to the secondary amine. In particular this side-reaction is reduced or virtually completely suppressed by the addition of bases. This also applies to the intramolecular imine formation, thus the formation of 2-aza-4,6,6-trimethyl-bicyclo[3,2,1]octane.

The addition may be made either before the imination of the isophorone nitrile or not until imination is complete or partially completed and before the hydrogenation. The addition of hydroxide bases can increase the isophorone diamine yield and/or increase the purity of the isophorone diamine. Suitable hydroxide bases are, for example, alkali hydroxides or alkaline earth hydroxides. Hydroxide bases which are particularly preferred are quaternary ammonium hydroxides. Suitable ammonium hydroxides are those corresponding to the general formula $(R^1R^2R^3R^4N)^+OH^-$, in which $R^1$ to $R^4$ may be the same or different, and stand for aliphatic, cycloaliphatic or aromatic radicals. Examples are tetramethyl-, tetraethyl-, tetra-n-propyl- and tetra-n-butylammonium hydroxide. Suitable concentrations are from 0.01 to 100 mmol, preferably 0.05 to 20 mmol of a tetraalkylammonium hydroxide per mole isophorone nitrile.

It is also possible to use one or more co-catalysts in the hydrogenation according to the invention of isophorone nitrile or isophorone nitrilimine with a hollow-body-form cobalt, nickel, copper and/or iron catalyst. Suitable co-catalysts are salts of cobalt, nickel, lanthanum, cerium or yttrium, preferably salts of cobalt and nickel. A preferred quantity of co-catalyst is around 0.01 to 0.5 mole, preferably 0.05 to 0.2 mole co-catalyst per mole cobalt, nickel, copper and/or iron catalyst. The co-catalyst(s) may be added in the form of anhydrous salts or salts containing water of crystallisation, in powder form, as a solution or as a suspension to the cobalt, nickel, copper and/or iron catalyst or to the reaction mixture.

It is also possible, but not preferred, to prepare isophorone diamine in single-stage process from isophorone nitrile by hydrogenation through to amine with a hollow-body-form cobalt, nickel, copper and/or iron Raney catalyst. In this process isophorone nitrile is converted in situ in the presence of ammonia into isophorone nitrilimine which is then hydrogenated further to isophorone diamine. The single-stage process is preferably carried out continuously in a fixed-bed reactor in the manner in which the reactor is used as a trickle-bed reactor (q.v., for example, EP 0 659 734).

The process according to the invention for the preparation of isophorone diamine from isophorone nitrile by hydrogenation through to amine has the following advantages: the hollow-body-form cobalt, nickel, copper and/or iron catalyst of the Raney type used according to the invention has a markedly lower bulk density than Raney catalysts used hitherto. As a result substantially less catalyst material is needed in the preparation of isophorone diamine than in the processes known hitherto.

Despite the markedly lower quantity of catalyst material, the preparation of isophorone diamine can be carried out with high conversion rates, very good yields and very good space-time yields.

Because less catalyst material is required the cost of engineering for the reactors utilised for the preparation of isophorone diamine is lower. This is due, for example, to the lower weight of the hollow-body-form cobalt, nickel, copper and/or iron catalyst.

EXAMPLES

Implementation Example

The catalysts are tested for catalytic activity in the preparation of 3-aminomethyl-3,5,5-trimethylcyclohexylamine (isophorone diamine, IPDA) from 3-cyano-3,5,5-trimethylcyclohexanone (isophorone nitrile, IPN) in a two-stage process. The process is substantially described in DE 195 40 191 C1.

In the first stage, isophorone nitrile is here converted at least partially with ammonia and with the addition of methanol into 3-cyano-3,5,5--trimethylcyclohexamine in the presence of an imination catalyst, and in the second stage is hydrogenated with hydrogen through to amine on a hydrogenation catalyst at a temperature of 100° C. and at a pressure of 6 MPa.

Deviating from the procedure described in DE 195 40 191 C1, each stage in the preparation of IPDA is carried out in separate reactors. The two reactors are, however, connected in series. They are temperature-controlled by separate oil heaters.

The first reactor tube has an internal diameter of 20 mm and a length of 250 mm and is charged with 30 ml of an organopolysiloxane which contains sulfonate groups (grain size from 0.4 to 1.4 mm; bulk density 525 g/l) as the imination catalyst (q.v. DE Patent Application No. 196 27 265.3).

The hydrogenation reactor has an internal diameter of 17 mm and a length of 350 mm and is charged with 150 ml of the respective catalyst to be tested in each test.

The temperature of the first reactor is adjusted to 35° C. and that in the second reactor to 100° C. The pressure in both reactors is 6 MPa.

The feed solution of IPN (15 wt. %), ammonia (30 wt. %) and methanol (55 wt. %) is pumped through the first reaction tube from below at a mass flow of 80 ml/h; the iminated reaction mixture obtained here runs thence to the second reactor. The hydrogen is introduced into the second reaction tube from above at a trickling volume flow rate of 36 l/h, the reactor therefore being operated as a trickle-bed reactor. The product liquid is caught below the reactor in a separating vessel.

The product mixture caught is examined by gas chromatography for IPDA and corresponding by-products. The results of the investigation are shown in Table 1.

Example 1

A coating solution is prepared by suspending 800 g of an alloy of 50% Co/50% Al in 1,000 ml aqueous solution containing 5 wt. % polyvinyl alcohol and 1.25 wt. % glycerol.

This suspension is then sprayed onto 2,000 ml polystyrene spheres in the approximately 2 mm range while they are suspended in an upwardly-directed air current. Following coating of the polystyrene spheres with the aforementioned solution the spheres are then dried in upwardly flowing air at temperatures of up to 80° C. (higher temperatures may also be applied). Half of these dried, coated polystyrene spheres are coated further with an alloy solution. The solution for the second layer comprises 800 g of an alloy of 50% Co/50% Al, which is suspended in 1,000 ml of an aqueous solution containing 5 wt. % polyvinyl alcohol and 1.25 wt. % glycerol. This suspension is then sprayed onto 1,000 ml of the aforementioned polystyrene spheres which were pre-coated with Co/Al and dried, while they are suspended in an upwardly directed air current. The second coating may also be effected with a different alloy containing different metals and/or having particles having different particle size distributions, such that the corresponding catalytic hollow sphere can show particular properties such as bimodal metal and/or pore distribution because of the particularly constructed coating.

Following coating of the polystyrene spheres with the aforementioned solution the spheres are then heated to 700° C. in a controlled nitrogen/air current in order to burn out the polystyrene and sinter together the alloy particles. The hollow spheres are then activated in a 20 wt. % sodium hydroxide solution for 1.5 hours at 80° C. The activated hollow spheres obtained have diameters within the region of about 3 mm, a mantle thickness of about 700 μm and a bulk density of 0.80 g/ml.

As may be observed visually from the evolution of hydrogen bubbles, the catalyst has a large reservoir of active hydrogen.

According to the aforementioned Implementation Example, testing of the activated cobalt hollow spheres (catalyst B1) for the preparation of IPDA showed an IPDA yield of 94.4% and an IPDA purity of 99.9% after working-up by distillation.

Comparison Example 1

A conventional commercial cobalt supported catalyst (Co on a silicate) is tested as a hydrogenation catalyst, in accordance with the aforementioned Implementation Example for the preparation of IPDA. After working-up by distillation according to Example 1, this catalyst (VB1) demonstrated an IPDA yield of 90.2% and an IPDA purity of 99.75%.

TABLE 1

| Catalyst | IPDA yield | IPDA purity |
|----------|-----------|-------------|
| B1       | 94.4      | 99.9        |
| VB1      | 90.2      | 99.75       |

What is claimed is:

1. A process for the preparation of isophorone diamine from isophorone nitrile, isophorone nitrilimine or mixtures containing isophorone nitrile and/or isophorone nitrilimine comprising hydrogenating an isophorone starting material selected from isophorone nitrile, isophorone nitrilimine or mixtures containing isophorone nitrile and/or isophorone nitrilimine to the corresponding amine in the presence of at least ammonia, hydrogen, hydrogen and a Raney catalyst, characterised in that the Raney catalyst is in the form of hollow bodies.

2. The process according to claim 1, wherein the process is carried out in two stages including a first stage in which isophorone nitrile is converted at least partially with ammonia into isophorone nitrilimine in the absence or in the presence of an imination catalyst and/or of an organic solvent, and a second stage in which the reaction mixture of the first stage is hydrogenated through to amine in the absence or in the presence of an organic solvent at a temperature within the range 20 to 150° C. and at a pressure within the range 0.3 to 50 MPa.

3. The process according to claim 1 wherein the Raney catalyst hollow bodies are hollow spheres.

4. The process according to claim 1 wherein the Raney catalysts have a bulk density within the range 0.3 g/ml to 1.3 g/ml.

5. The process according to claim 1 wherein the catalysts bodies used have a diameter within the range 0.5 to 20 mm.

6. The process according to claim 1 wherein the catalyst bodies used have a shell thickness within the range 0.1 to 7.0 mm.

7. The process according to claim 1 wherein the catalyst bodies used in the process contain no binder.

8. The process according to claim 1 wherein the catalyst bodies used in the process contain an inorganic binder.

9. The process according to claim 1 wherein the cobalt, nickel, copper and/or iron catalyst is doped with elements from Groups 3B to 7B, 8 and 1B of the Periodic Table, in particular chromium, manganese, iron, vanadium, tantalum, titanium, tungsten, molybdenum, rhenium and/or metals in the platinum group.

10. The process according to claim 1 wherein the cobalt, nickel, copper and/or iron catalyst is doped with elements from Groups 1A, 2A, 2B, and/or 3A of the Periodic Table and/or germanium, tin, lead, antimony and/or bismuth.

11. The process according to claim 2 wherein the imination of isophorone nitrile is in the presence of an imination catalyst and/or an alcohol and/or ether.

12. The process according to claim 2 wherein the hydrogenation through to amine is carried out in a fixed-bed reactor or suspension reactor in continuous operation.

13. The process according to claim 12 wherein the hydrogenation through to amine is carried out in the trickle-bed process, where the reactor or reactors are connected in series and the reaction mixture which is to be hydrogenated through to amine runs through one or more temperature stages arranged with increasing temperatures.

14. The process according to claim 2 wherein a co-catalyst from the series of a cobalt or nickel salt is present.

15. The process according to claim 2 wherein hydrogen is not added in excess.

16. The process according to claim 2 wherein the entire process or individual stages of the process are carried out in the batch process.

17. The process according to claim 1 wherein a basic material, preferably an alkali hydroxide, alkaline earth hydroxide or ammonium hydroxide, is present.

18. The process according to claim 1 wherein the process is carried out in two stages, including a first stage in which isophorone nitrile is converted at least partially with ammonia in the absence or in the presence of an imination catalyst and in the absence of an organic solvent into isophorone nitrilimine, and a second stage, in which the reaction mixture of the first stag is hydrogenated through to amine in the absence of an organic solvent at a temperature within the range 60 to 150° C. and at a pressure within the range 5 to 50 MPa.

19. The process according to claim 1 wherein the Raney hydrogenation catalyst is based on nickel.

20. The process according to claim 1 wherein the Raney hydrogenation catalyst is based on copper and/or iron.

21. The process according to claim 1 wherein the Raney hydrogenation catalyst is based on cobalt.

* * * * *